(12) United States Patent  (10) Patent No.: US 7,481,125 B2
Mayeaux  (45) Date of Patent: Jan. 27, 2009

(54) DEVICES FOR OBTAINING CYLINDER SAMPLES OF NATURAL GAS OR PROCESS GAS, AND METHODS THEREFORE

(76) Inventor: Donald P. Mayeaux, 13136 Bayou Terrace Dr., St. Amant, LA (US) 70775

( * ) Notice: Subject to any disclaimer, the term of this patent is extended or adjusted under 35 U.S.C. 154(b) by 142 days.

(21) Appl. No.: 11/151,018

(22) Filed: Jun. 13, 2005

(65) Prior Publication Data

US 2005/0257631 A1 Nov. 24, 2005

Related U.S. Application Data

(60) Continuation-in-part of application No. 10/408,026, filed on Apr. 3, 2003, now Pat. No. 6,904,816, which is a division of application No. 09/915,192, filed on Jul. 25, 2001, now Pat. No. 6,701,794, and a continuation-in-part of application No. 09/162,239, filed on Sep. 28, 1998, now Pat. No. 6,357,304, which is a continuation-in-part of application No. 08/701,406, filed on Aug. 22, 1996, now Pat. No. 5,841,036, application No. 11/151,018, which is a continuation-in-part of application No. 10/631,501, filed on Jul. 31, 2003, now Pat. No. 7,225,690.

(60) Provisional application No. 60/400,736, filed on Aug. 2, 2002, provisional application No. 60/221,335, filed on Jul. 26, 2000.

(51) Int. Cl.
  *G01N 1/22* (2006.01)
  *G01N 1/20* (2006.01)
  *G01N 1/12* (2006.01)

(52) U.S. Cl. .............. 73/864.62; 73/863.52; 73/863.57; 73/863.11; 73/863.84; 73/864.63

(58) Field of Classification Search . 73/863.81–863.86, 73/863.11, 864.62, 864.63, 863.52, 863.57, 73/864.34

See application file for complete search history.

(56) References Cited

U.S. PATENT DOCUMENTS 3,203,247 A * 8/1965 Bicek ...................... 73/864.91

(Continued)

FOREIGN PATENT DOCUMENTS

DE 3310032 A1 * 9/1984

(Continued)

OTHER PUBLICATIONS

NB9103334, Discrete Depth Groundwater Sampler, Sample Container And Monitor. Mar. 1, 1991, IBM Technical Disclosure Bulletin, vol. No. 33, Issue No. 10B, p. No. 334-335.*

(Continued)

*Primary Examiner*—Thomas P Noland

(57) ABSTRACT

A sample pump system for metering the amount of sample taken from a pressurized fluid process such as a natural gas pipeline or the like, the sample pump system designed for immersion, directly or indirectly, into the pressurized fluid stream so that the sampling is taken at the prevailing pressure and temperature of the fluid stream. A spot sample cylinder device is further provided which employs a method of collection wherein the initial cylinder volume of the collection vessel or sampling cylinder is zero. The spot sample cylinder is inserted into the pressurized gas (or fluid) source, said sample cylinder employing a piston or moveable end configured such that purging of the cylinder sample cavity is not required, since the sample cavity volume is essentially eliminated prior to sampling by the location of the piston within the cavity, the cavity expanding upon sampling via piston movement within the cavity.

32 Claims, 5 Drawing Sheets

U.S. PATENT DOCUMENTS

| | | | | |
|---|---|---|---|---|
| 3,273,647 | A | * | 9/1966 | Briggs, Jr. et al. ........... 166/100 |
| 3,831,953 | A | * | 8/1974 | Leibfritz et al. ............. 277/180 |
| 3,835,710 | A | * | 9/1974 | Pogorski ................... 73/864.74 |
| 3,848,579 | A | * | 11/1974 | Villa-Real ................... 600/577 |
| 3,872,721 | A | * | 3/1975 | Ilfrey ...................... 73/152.28 |
| 4,014,216 | A | * | 3/1977 | Thornton et al. ......... 73/863.23 |
| 4,112,768 | A | * | 9/1978 | Holland et al. ........... 73/863.24 |
| 4,157,040 | A | * | 6/1979 | Barton et al. ............ 73/863.23 |
| 4,800,763 | A | * | 1/1989 | Hakkers et al. ............... 73/863 |
| 4,821,585 | A | * | 4/1989 | Kempe .................... 73/863.23 |
| 4,865,811 | A | * | 9/1989 | Newton et al. ................ 422/81 |
| 4,928,541 | A | * | 5/1990 | Toon et al. ................ 73/864.63 |
| 4,974,456 | A | * | 12/1990 | Ortiz et al. ............... 73/863.52 |
| 5,205,988 | A | * | 4/1993 | Tanaka et al. ................. 422/91 |
| 5,442,969 | A | * | 8/1995 | Troutner et al. .......... 73/863.71 |
| 5,536,474 | A | * | 7/1996 | Ungerer et al. ........ 73/864.62 X |
| 5,637,792 | A | * | 6/1997 | Kimura et al. ................ 73/116 |
| 5,794,695 | A | * | 8/1998 | Peterson ..................... 166/264 |
| 5,814,741 | A | * | 9/1998 | Wang et al. .............. 73/863.12 |
| 5,844,123 | A | * | 12/1998 | Marsh et al. ............. 73/863.12 |
| 6,659,177 | B2 | * | 12/2003 | Bolze et al. ................. 166/264 |
| 6,793,819 | B2 | * | 9/2004 | Glenwright et al. ... 73/863.84 X |
| 2003/0089526 | A1 | * | 5/2003 | Beeker ........................ 175/58 |
| 2003/0103551 | A1 | * | 6/2003 | Haddad et al. .............. 374/136 |

FOREIGN PATENT DOCUMENTS

| | | | | |
|---|---|---|---|---|
| JP | 6-288880 | * | 10/1994 | .................. 73/863 |
| SU | 1250251 A | * | 8/1986 | |
| SU | 1520382 A | * | 11/1989 | |
| WO | 95/02176 | * | 1/1995 | |

OTHER PUBLICATIONS

A+ Corporation, "Series 100 Genie Membrane Separators", Aug. 1998, pp. 1-7.*

Manual of Petro Meas Stds Ch. 14, Sec 1, Collecting and Handling of Natural Gas Samples for Custody Transfer, API (4th Ed, Aug. 1993), pp. 2, 3, 6, and 12.

Technical Memorandum—Metering Research Facility Program; Gas Research Institute, Transmission Operations, Apr. 1998, pp. 32-33.

The Calibration Station (Newsletter of Colorado Engineering Experiment Station, Inc.) vol. 1, Fall Winter 1997, pp. 1-2.

Welker, Thomas F., Sample Conditioning, 1997 Proceedings of AM SCH of Gas Measurement Tech, pp. 79-81.

Ting, V.C., Effect of Entrained Liquid on Orifice Measurement, Sep. 1998, Proceedings of AM Sch of Gas Measurement Tech, pp. 85-88.

A+ Corp, Prairieville, LA Series 100 Genie Membrane Separators Brochure, Rev Aug. 1998, pp. 1-7.

A+ Corp, Prairieville, LA Series 200 Genie Membrane Separators Brochure, Rev Mar. 1996, pp. 1-6.

* cited by examiner

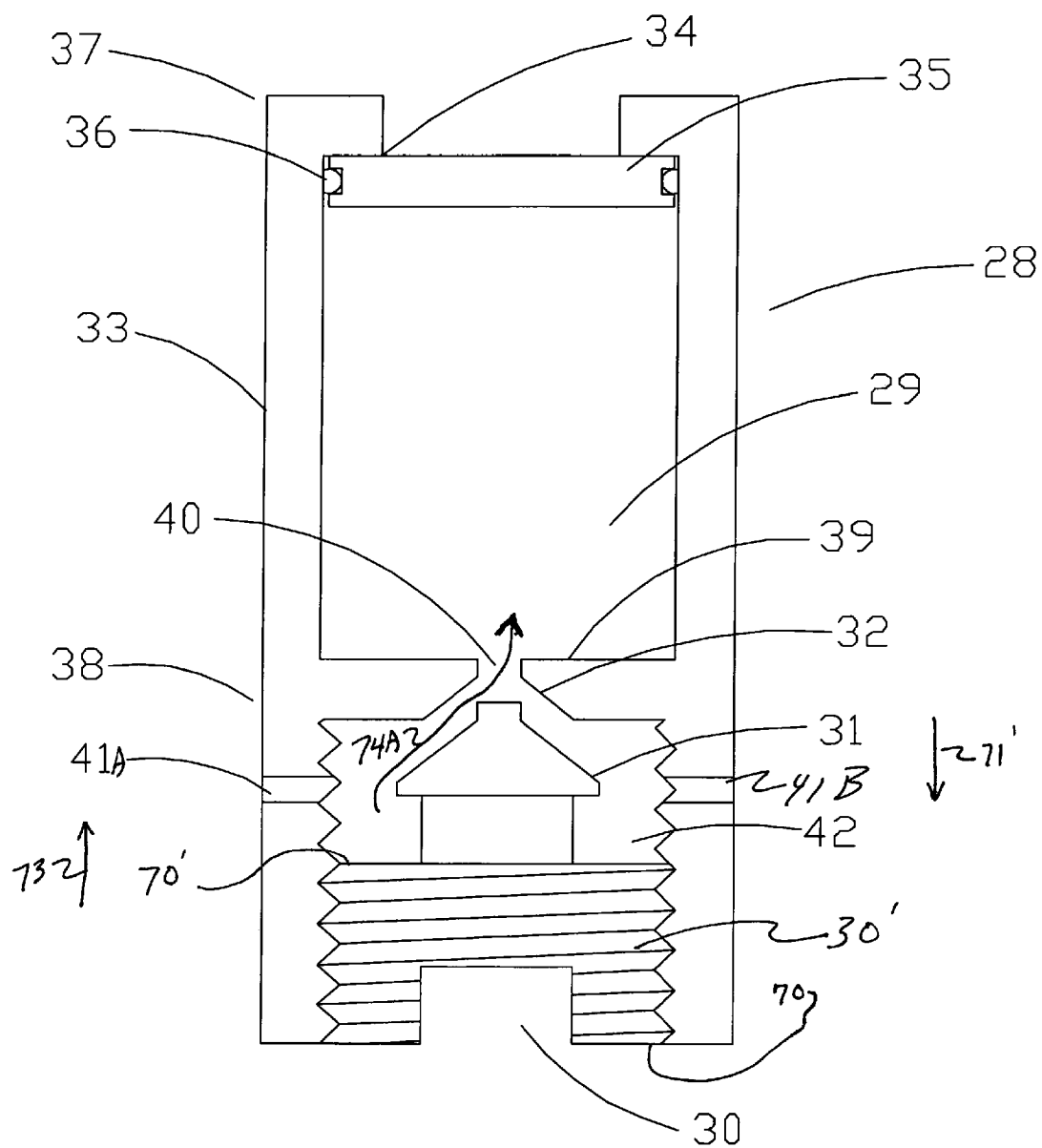

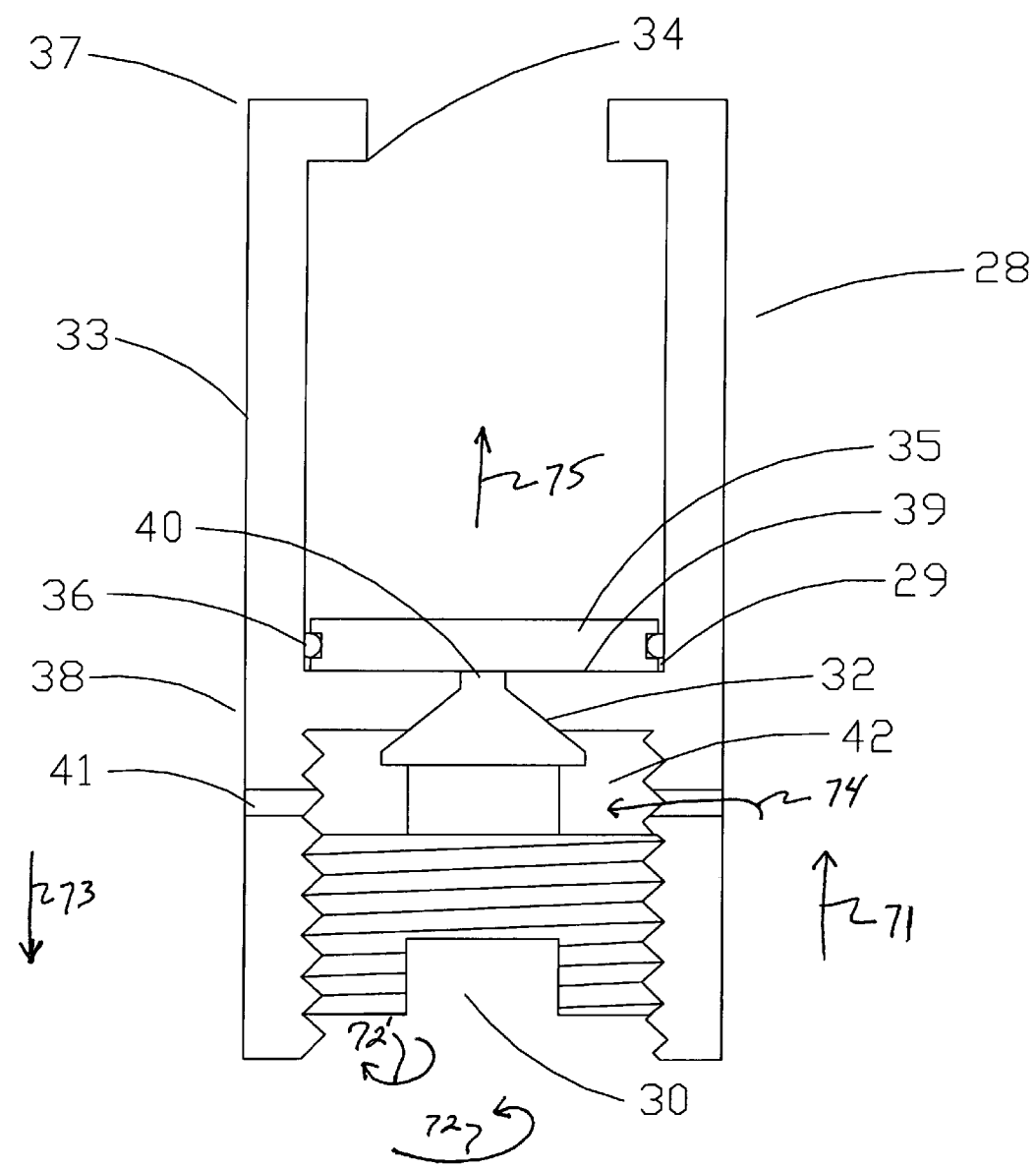

DEVICES FOR OBTAINING CYLINDER SAMPLES OF NATURAL GAS OR PROCESS GAS, AND METHODS THEREFORE

DOMESTIC PRIORITY DATA AS CLAIMED BY APPLICANT

The present application claims the benefit of Provisional Application 60/646,314 filed Jan. 24, 2005 entitled "Devices for Obtaining Cylinder Samples of Natural Gas or Process Gas".

The present application is also a continuation in part of U.S. patent application Ser. No. 10/408,026 filed Apr. 3, 2003, now U.S. Pat. No. 6,904,816, which is a divisional of U.S. patent application Ser. No. 09/915,192 filed Jul. 25, 2001, now U.S. Pat. No. 6,701,794, which claims the benefit of Provisional Application 60/221,335 filed Jul. 26, 2000, and is a continuation in part of Ser. No. 09/162,239 now U.S. Pat. No. 6,357,304, having a filing date of Sep. 28, 1998, which is a continuation in part of U.S. patent application Ser. No. 08/701,406, now U.S. Pat. No. 5,841,036, filed Aug. 22, 1996.

The present application is also a continuation in part of U.S. patent application Ser. No. 10/631,501 filed Jul. 31, 2003, now U.S. Pat. No. 7,225,690 entitled "Multi-Cavity Sample Cylinder with Integrated Valving", which claims the benefit of Provisional Application 60/400,736 having a filing date of Aug. 2, 2002.

TECHNICAL FIELD OF THE INVENTION

The present invention relates to composite samplers or the like for analytical fluid testing as in the petrochemical industry, and in particular to a sample pump system for metering the amount of sample taken from a pressurized fluid process such as a natural gas pipeline or the like, the sample pump system designed for immersion, directly or indirectly, into the pressurized fluid stream so that the sampling is taken at the prevailing pressure and temperature of the fluid stream.

To further enhance the technique of the present invention, device is provided which employs a method of collection is utilized wherein the initial cylinder volume of the collection vessel or sampling cylinder is zero. A spot sample cylinder is inserted into the pressurized gas (or fluid) source, said sample cylinder employing a piston or moveable end to configured such that purging of the cylinder sample cavity is not required since the sample cavity volume is eliminated prior to sampling, the cavity expanding upon sampling.

BACKGROUND OF THE INVENTION

In many cases the cost of installing an "on line" analyzer for a natural gas or other process stream cannot be justified. In such cases, a "spot" sample is taken periodically, or a composite sample is taken over a period of time. A "spot sample" generally consists of extracting a sample of the gas at a "spot", or single point in time.

A composite sample is generally taken by a sampling apparatus (composite sampler) which extracts a small volume (bite) of gas sample periodically, which is collected in a sample cylinder. A typical composite sampler will control the sampling interval based on time or flow volume. Flow volume information, or electric pulse, is usually provided by an external flow computer. A typical composite collection period is 30 days. There are two basic types of sample cylinders utilized for spot and composite sampling. They are the constant volume and constant pressure types of sample cylinder. Constant pressure types of sample cylinders are of the floating piston or bladder (bag) type.

Gas Processors Association Standard Publication 2166 entitled "Obtaining Natural Gas Samples for Analysis by Gas Chromatography" details several spot sampling methods in its 1986 revision and its draft. The main thrust of the GPA 2166 standard deals with methods for purging the sample cylinder, dealing with entrained liquid using the GPA or other type separator, and prevention of condensation of gas components. The draft copy addresses major errors in the 1986 revision. In particular, it dwells on the use of external separator to remove liquids at other than the source gas conditions of pressure and temperature.

American Petroleum Institute Manual of Petroleum Measurement Standards, Chapter 14, Section 1, revised in 2001, the contents of which are incorporated herein by reference, addresses spot and composite sampling issues. It is critical of the GPA 2166-1986 standard, in particular, the use of an external separator such as the GPA separator, for removing entrained liquids (refer to 14.1.8.7). The API 14.1 standard-rev 2001, is based on research work done by Southwest Research Institute.

The hydrocarbon dew point temperature (HCDPT) and its impact on the sampling of natural gas is the main focus of the API 14.1 standard. This is evident in the opening paragraph "14.1.1 Introduction". Refer to 14.1.6, here the standard calls out issues which need to be addressed when sampling natural gas. Issues include ambient temperature condition and phase-change characteristics. In 14.1.6.6, it makes clear that no part of the spot or composite sampling system should be allowed to fall below the HCDPT, otherwise biased analytical results and non-representative samples are likely to result. Maintaining the sample system at, or above, the HCDPT is recommended.

In 14.1.6.6.4 (Sample containers), it states that the cylinder temperature must be kept above the HCDPT. Note that the author is a member of the API 14.1 working group responsible for the writing the standard. The reason that the recommendation is for the cylinder temperature to be "above" as opposed to "equal to or above" the HCDPT is due to the uncertainty of measuring the HCDPT. It is well known, from a thermodynamic standpoint, that maintaining a gas at the HCDPT will not yield condensation.

Referencing the 14.1.6.6.6 composite sampling systems in the above publication, in short, it recommends that these systems, including the containers, (a direct quote) be maintained above the HCDPT to ensure that the composite sample is representative of the flowing gas stream. Similar references are made in 14.1.13.1.1.

REFERENCES

1. Gas Processors Association (GPA) standard 2166-1986 and draft copy of 2166-2004
2. API manual of Petroleum measurement standards chapter 14, section1, collecting and handling of natural gas samples for custody transfer. API-14.1 revision 2001
3. Southwest Research Institute (SRI) San Antonio, Tex.
4. Accuracy of Natural Gas Sampling Techniques, and the impact of composition measurement errors on Flow Rate and Heating value determination. By K. A. Behring II, Southwest Research Institute. Paper presented at Flomeko '98, International conference on Flow Measurement, (Lund, Sweden, Jun. 15-17, 1998)

The entire API 14.1-2004 document is rich in thermodynamic and practical information. For example, in Appendix A, "The Phase Diagram" and A.1 Phase changes in general. In referring to the API 14.1-2004 document, especially its Appendix A and to the paper "Accuracy of Natural Gas Sampling Techniques, and the Impact of Composition Measurement Errors on Flow Rate and Heating Value Determination", K. A. Behring, Flomeko '98, the 9th Int Conf on Flow Measurement, Lund, Sweden (Jun. 15-17, 1998), one can conclude that condensation of portion of a gas phase and/or vaporization of a liquid wherein the resulting vapor becomes intermixed with the gas phase will likely (almost certainly) result in product composition changes in the gas phase.

It is well known and understood that even small changes in the composition of a natural gas sample can have a significant impact on its heating value (BTU content) and other important physical properties some of which are utilized for making flow rate calculations. The heating value and flow rate (volume) of the natural gas are key factors in determining its monetary value.

In summary, the cost of adhering to the API 14.1 and GPA 2166 standards, in particular the cost and attention required to maintain all parts of the prior art sampling system and cylinders above the HCDPT, results in the very frequent improper sampling of natural gas. Even small changes made to the current and prior art sampling procedures often result in inaccurate, non-representative samples.

The problems are primarily due to the current art of having the sample conditioning system and the sample containment cylinders external to the vessel or pipeline. Spot and composite sample have traditionally been taken in that manner ever since spot and composite samples were first taken. This requires the use of costly equipment, especially in cold climates and/or wet gas (high HCDPT) applications.

GENERAL SUMMARY DISCUSSION OF THE INVENTION

The present invention overcomes the expense and reliability problems associated with the above prior art techniques, in the case of spot sampling, by inserting the cylinder inside of the pressurized containment vessel or pipeline when taking a sample.

In the case of the composite sampler, the system of the present invention inserts the "sample pump" (which meters the small sample bites via positive displacement of the components, as opposed to a check valve) into the pressurized containment vessel or pipeline during the sampling period. By having the spot sampling pump or spot sampling cylinder inside of the gas (or fluid) source the bulk (if not all) of the traditional sample conditioning components are eliminated. Further, purging of the sample train is eliminated.

To further enhance the technique of the present invention, a method of collection is utilized wherein the initial cylinder volume of the collection vessel or sampling cylinder is zero. Such is the case if the "Flexible isolation barrier"(FIB) type of cylinder is utilized, such as taught in co-pending Mayeaux patent application Ser. No. 10/631,501, filed Jul. 31, 2003, entitled "multi-cavity sample cylinder with integrated valving", the contents of which are incorporated herein by reference. In that case, a small cylinder, containing a Flexible isolation barrier (FIB), is inserted into the gas source. Sample valving design differs from that referenced in the patent application for the multi cavity cylinder, since the filling operation differs.

In a second case, a spot sample cylinder is inserted into the pressurized gas (or fluid) source, said sample cylinder having a movable end (M.E.) (FIGS. 4 and 5). Both, the FIB and M.E. approach do not require purging of the cylinder sample cavity since in both cases the sample cavity volume is essentially zero. Being inserted into the fluid process to be sampled eliminates the typical fluid sample extraction, transporting and conditioning system which of course eliminates purging of that type system.

It is noted here that the term "sampling cylinder" is not intended to limit the structure to sampling, but can be used for other purposes, such as collection and storage. Accordingly, "sampling cylinder" or the like should be considered in the present disclosure as synonymous with storage cylinder, collection cylinder, or like devices.

By allowing the sample gas to flow through a phase separation membrane designed to reject liquids (all types) and particles before entering the sample cylinder (micro cylinder), entrained liquids are eliminated. The separated liquid can either be drained back into the pressurized process, or captured for analysis or the like.

Therefore, by inserting said micro cylinder into the fluid process, said micro cylinder or other sample cylinder having a "zero sample cavity volume" at the beginning of a sampling procedure, and eliminating liquids and particles from the sample gas entering the micro cylinder, the three largest sources of error in spot sampling are eliminated.

Preventing vapor/liquid equilibrium changes (which alter the gas phase composition) is accomplished by sampling at the prevailing source fluid conditions of pressure and temperature, since the cylinder is immersed "in" the fluid source.

Removing entrained liquids (in the case of gas sources such as natural gas) by using a phase separating membrane, which rejects liquids while allowing gases and vapors to flow through, eliminates the equilibrium changes by sampling only the gas phase of the fluid source at the prevailing pressure temperature conditions of the gas source. Particles are removed with the phase separating membrane and/or any other type of suitable particulate filter prior to entry into the sample cylinder.

The "zero volume sample cavity" (FIB, movable end or any other zero volume sample cavity) eliminates the need for purging the cylinder, which said cylinder purging represents one of the largest and most frequent sources of analytical error in the sampling of natural gas. An alternate means for eliminating the purging step is to evacuate the sample cylinder (micro cylinder) prior to the sampling process.

Specific mechanical designs for devices to insert the MC into a pressurized fluid process utilizing the dynamic sealing and pressure equalization will follow.

In the case of "composite sampling" the solution is to insert the "sample pump" into the fluid process to be sampled. The impact of the ambient temperature on the sample conditioning system and sample pump for the composite sampler is eliminated. The process of composite sampling is greatly simplified. As with spot sampling, the principle sources of error are eliminated.

By having the sample pump inserted into the process in a manner which insures that the pump is at essentially at the fluid process temperature, errors are eliminated which would result from condensation. Additionally, by allowing the sample gas to first flow through a phase separating membrane to reject and remove all liquids, errors associated with phase equilibrium changes are eliminated.

In the case of spot and composite sampling inventions (i.e. the "micro cylinder" and the "insertable pump") purging is eliminated or substantially reduced, thus releases of process fluid to the atmosphere is reduced in the same proportion.

In operation the "insertable pump" (IP), in each complete sample injection cycle, captures a small volume of sample fluid (inject volume) and moves (pumps) it into a sample container (cylinder). The frequency of each cycle was previously discussed.

It is imperative that the temperature and/or pressure of the sample fluid are not changed from the original (prevailing conditions of the source fluid) in a manner which would either promote condensation or vaporization to occur (i.e. produce a phase change—said phase change being gas to liquid or vice versa) for reasons preciously discussed and referenced.

However, once the "sample pump" has captured a sample volume (i.e. isolated it from the fluid process) phase changes will not produce errors or alter the overall sample (liquid and gas together) composition, providing that all of the captured sample volume (including gas and liquid) is sent, pumped, or transported in any manner to a sample container or cylinder.

Testing performed at SRI has shown that by appropriate heating of a sample cylinder liquid can be vaporized and re-homogenized with the gas phase to produce a uniform gas phase adequate for analysis and representing the original composition before liquification (i.e. condensation) occurred. The main reason that condensation usually produces changes in a sample gas is that the liquid is not re-associated with its former gas phase.

This is prone to occurring in a flowing sample. However when all or essentially all of the gas and liquid formerly associated with it remain associated (i.e. are stored together) and especially when stored in a common volume such as is the case in a sample cylinder, it can be re-vaporized, homogenized and reconstituted to its original composition. Note that it is recommended by both API 14.1 and GPA 2166 that sample cylinders are heated for some time prior to analysis, for the specific purpose of re-vaporizing liquids which may have condensed after the sample was taken.

To effectively transfer essentially all liquid and gas measured and/or captured by the sample pump (insertable pump) from the pump to a sample cylinder external to the pressurized source the transfer tubing or fluid passageway must be of a small diameter. A small diameter is desirable for two reasons. First there is less fluid trapped between the pump and sample cylinder, and secondly liquid cannot remain trapped in the lower segments of the passageway. A suitable diameter for such a passageway is 0.032 to 0.062 inches diameter.

The insertable pump may be inserted into a fluid process if the process is depressurized or inserted while the process in pressurized by several means. Dynamic seals and/or pressure balance techniques previously discussed may be employed to insert the pump without altering the spirit of the invention.

Multiple inventions are contemplated in the present case. These inventions require the functional elements to be inserted into a pressurized fluid process. All of the inventions capture sample fluids.

In one invention, the micro cylinder, a single sample cycle results in the filling of a sample cavity with sample fluid. In the other invention, in a single sample cycle a pump (the insertable pump) meters out (captures) a volume of sample fluid and transfers (pumps) said sample fluid to a separate sample container (cylinder). Many sample cycles are completed, in general, to completely fill a sample cylinder or container, such cycles being executed over a significant time period (typically 30 days).

In both cases, a constant volume or constant pressure sample cylinder may be utilized without altering the general spirit of the inventions.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 4 is a side, a partially cut-away, partially cross-sectional view of an exemplary design for a micro-cylinder for use in the present invention, wherein the moveable end is shown at the first end of the sample cavity.

FIG. 5 is a side, partially cut-away, partially cross-sectional view of the device of FIG. 4, wherein the moveable end is shown at the second end of the sample cavity.

DETAILED DISCUSSION OF THE INVENTION

Figure 1:
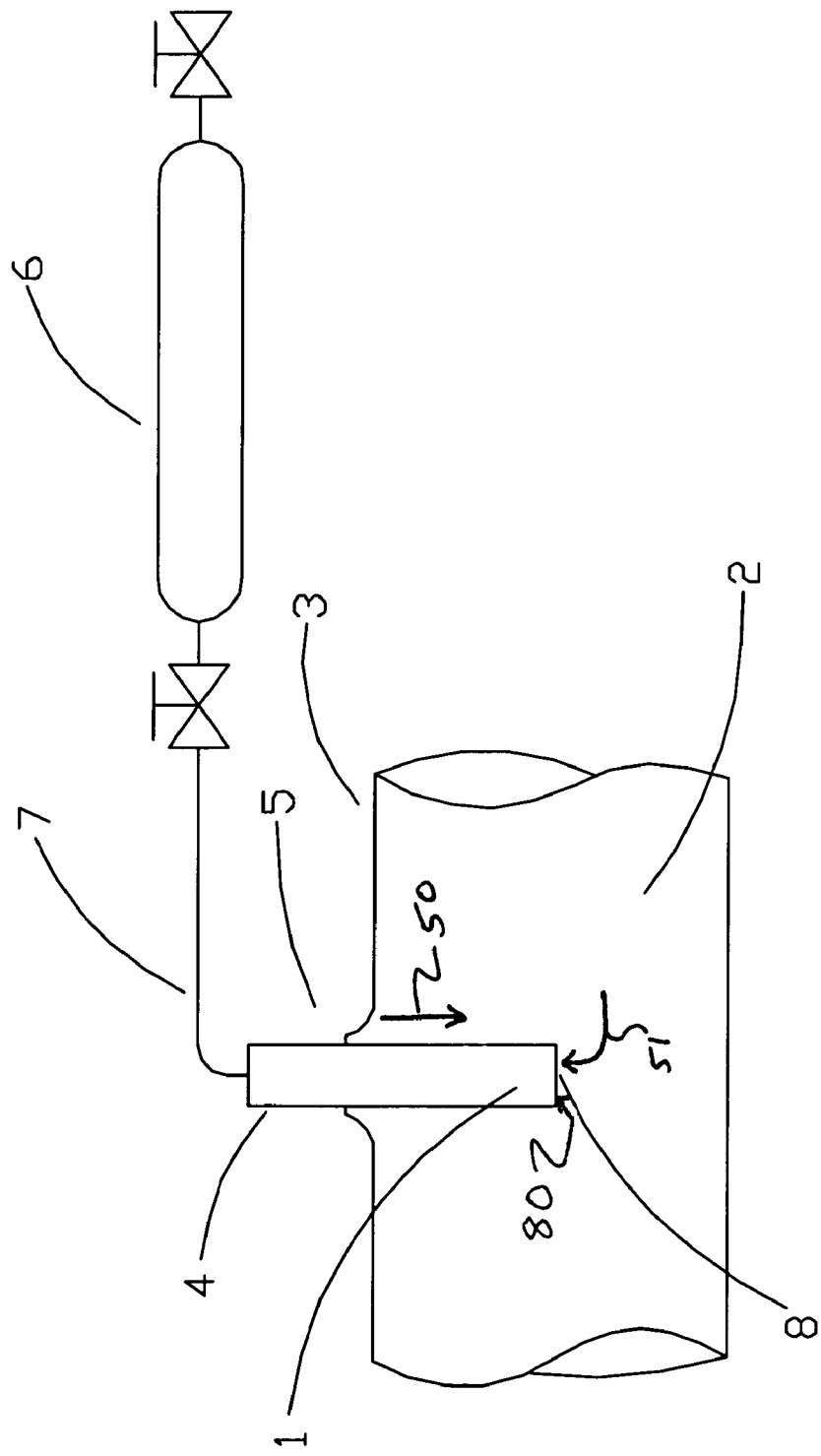
FIG. 1 is a diagram illustrating the components and operation of an insertable composite sampler pump installation of the present invention, in a pressurized fluid system.

FIG. 1 provides an overview of Insertable Composite Sampler Pump Installation into a Pressurized Fluid System.

As shown, the first end of an insertable composite sampler pump 1 is immersed 50 in the pressurized fluid process 2, such that both are essentially the same temperature. In operation, pressurized sample fluid 2 flows 51 into entry port 8, then into the first end of the insertable composite sampler pump (1) wherein a small volume is metered (captured). Said metered volume is then transferred (pumped) to storage or sample fluid cylinder (6) by way of transfer line (7).

This process (cycle) is repeated until the desired amount of sample fluid is captured and transferred to the sample fluid container (6), or until the desired time period is over for ending the process.

As earlier indicated, one may provide a phase separation membrane 80 designed to reject liquids (all types) and particles from the sample gas before entering the sample cylinder (micro cylinder) or sample pump, thereby eliminating entrained liquids from any sample obtained.

Pump Design Notes:

A composite sampler pump design is contemplated which could function as a current art, externally mounted composite pump. The design, however, is also well suited for insertion into a pressurized fluid source in the manner disclosed above.

Figure 3:
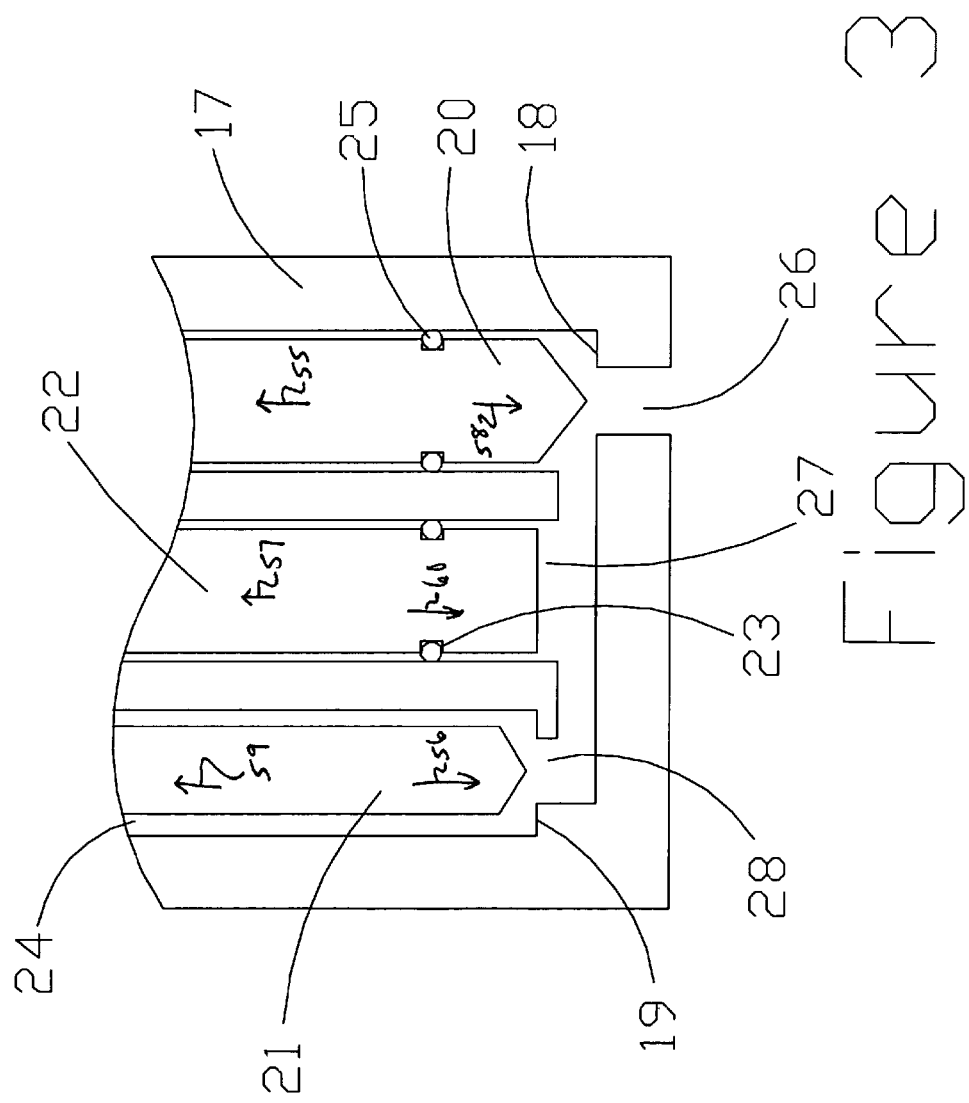
FIG. 3 is a side, partially cut-away, partially cross-sectional view of a preferred embodiment of the composite sampler pump of the present invention which could be used as an internally or externally mounted composite pump.

Referring to FIG. 3, the pump is comprised of a housing 17, intake valve seat 18, outlet valve seat 19, intake valve stem/poppet 20, outlet valve stem/poppet 21, displacement piston 22, piston seal 23, annulus/passageway 24, intake valve stem seal 25, intake port 26, and outlet port 28.

This design differs from the typical pumps used for this purpose in that the intake (or inlet) and outlet valves are positively actuated by an external force, as opposed to the flowing fluid and fluid pressure as is the case with a check-valve type of pumping operation. This positive displacement design allows better metering control, i.e. the intake valve can be shut off before the metered volume is displaced to an external container. Additionally, it eliminates intake valve Joules-Thompson cooling which otherwise can result in condensation of liquids.

The design of FIG. 3 contemplates actuation (which can comprise, for example, electric, hydraulic, pneumatic, or other actuation means) external to the pump for intake valve stem/poppet 20, outlet valve stem/poppet 21, and displacement piston 22.

In operation, fluid enters intake port 26 with intake valve stem/poppet 20 in the "up" or open position 55, outlet valve stem/poppet 21 in the down 56 or closed position as displacement piston 22 is retracted upward 57 to a point then stopped. Inlet valve stem poppet 20 is then actuated closed (lowered 58 against intake valve seat 18), outlet valve stem/poppet 21 is actuated open (raised 59 above outlet valve seat 19), and displacement piston 22 is actuated (lowered 60) to its lower position, thereby displacing fluid from metering chamber 27, through outlet port 28 and annulus/passageway 24 to an external container. A preferred size for the passageway width or diameter could comprise, for example, between 0.010" and 0.062".

After displacement piston 22 reaches its maximum downward travel distance then outlet valve, stem/poppet 21 is lowered 56 against outlet valve seat 19, thereby closing the outlet valve formed by outlet valve stem/poppet 21 and outlet valve seat 19.

As indicated, contemplated actuation means are pneumatic, hydraulic and/or linear electric motors, or conventional rotating type electric motors coupled to a gear train to produce the required up/down actuation movement of the inlet valve, outlet valve, and displacement piston.

A contemplated micro cylinder is shown in FIGS. 4 and 5. The micro cylinder 28 is comprised of a cylinder wall 33, having a mechanical end stop 34 at a first end 37, valve seat 32 at a second end 38, valve stem/poppet 31 mounted to threaded plug 30', movable end 35, seal 36, Hex recess 30, sample cavity 29, and valve 40 formed by valve stem/poppet 31 and valve seat 32 situated in valve chamber 42. Fluid flow passages 41A, 41B allow fluid from into valve chamber 42.

As shown, moveable end 35 slidingly engages the inner wall of sample cavity 29 to form a sliding barrier which is fluid sealed or fluid impermeable via seal 36, which can comprise, for example, an o-ring.

In the exemplary embodiment, valve chamber 42 has an inner wall forming a threaded connection for threadingly engaging threaded plug 30' having first 70 and second 70' ends, the first end 70 having hex recess 30 formed therein, the second end 70' having valve stem/poppet 31 engaged thereto.

As shown in FIG. 4, moveable end 35 is at first end 37 against mechanical stop 34 and valve stem/poppet 31 is retracted from valve seat 32. In this position, sample cavity 29 is at its maximum volume and valve 40 is opened.

In FIG. 5, moveable end 35 is at second end 38 against mechanical stop 39 and valve 40 is in the closed position, wherein the stem/poppet 31 is seated to valve seat 32. In this position, sample cavity 29 is at its minimum volume or essentially zero volume. Thus, the sample cavity provides a variable volume dependent upon the location of the mechanical stop relative to the first 37 and second 38 ends.

The micro cylinder (MC) may be inserted into a pressurized fluid source for obtaining a sample by a number of means. One such means utilizes a packing gland or dynamic pressure seal type of insertion device, similar to that used for insertion of probes, sensors, corrosion coupons etc. A second type of insertion means to insert the MC into a pressurized process utilizes a pressure balance approach similar to that described patent application Attorney Docket number MAYED05/11 by Mayeaux entitled "Portable Insertable Probe assembly", the contents of which are incorporated herein by reference.

Referring to FIGS. 4 and 5, with the moveable end 35 at the minimal volume position (as in FIG. 5), but with the valve closed (as in FIG. 4), the micro cylinder is inserted 71 into a pressurized fluid source for sampling. Threaded plug 30' may then be turned 72 in a first direction via hex recess 30 to open 73 valve 40 (as in FIG. 4), so as to allow fluid from the pressurized fluid source to migrate through 74 passages 41A, 41B into valve chamber 42, through the open 73 valve, and into 74A sample cavity 29, where moveable end 35 (FIG. 5) is slidingly urged 75 from the second end 38 to the first end 37 via pressure from the fluid entering the sample cavity 29, filling sample cavity with fluid, as movable end 35 migrates to the first end 37. Once the sample cavity has reached the first end 37, and is thereby filled, the threaded plug 30 may be turned 72' a second direction via hex recess 30 to close 73' valve 40, capturing and retaining the fluid in the sample cavity, thereby providing a filled micro cylinder, which may be then removed 71' from the pressurized fluid source for analysis or other purpose.

With the micro cylinder inserted into the pressurized fluid source, the above sample has been taken at prevailing temperature and pressure, providing an accurate sample of the contents of the pressurized fluid source.

A method of using the micro cylinder of the present invention may thereby be summarized as follows:

a. providing a spot sample container, comprising:
   a housing having formed therein a sample cavity having first and second ends, and a wall;
   a moveable end slidingly engaging said wall of said sample cavity, so as to form a moveable fluid barrier within said sample cavity, having a variable volume associated with the position of said moveable barrier;
   a valve associated with said sample cavity;
b. immersing said container into a pressurized fluid process;
c. allowing the temperature of said container to adjust to the temperature of said pressurized fluid process;
d. opening said valve;
e. allowing fluid from said pressurized fluid process to migrate into said sample cavity;
f. allowing said moveable stop to slidingly migrate from said first end of said sample cavity to said second end of said sample cavity as said sample cavity fills with fluid;
g. closing said valve, providing a filled spot sample container
h. removing said filled spot sample container from said pressurized fluid process.

It is noted that the micro cylinder or other sample container may be evacuated prior to use to insure non-contamination of the sample cavity. Evacuation of the sample cylinder prior to the sampling process eliminates the necessity of a moveable fluid barrier to selectively provide zero volume in the exemplary method illustrated in steps a-h, above. Alternatively, an inert gas, such as helium or the like, may be provided at a pressure less than the process fluid to prevent contamination prior to sampling. A constant volume or constant pressure sample cylinder may also be utilized in lieu of the moveable wall design of FIG. 4.

Figure 2:
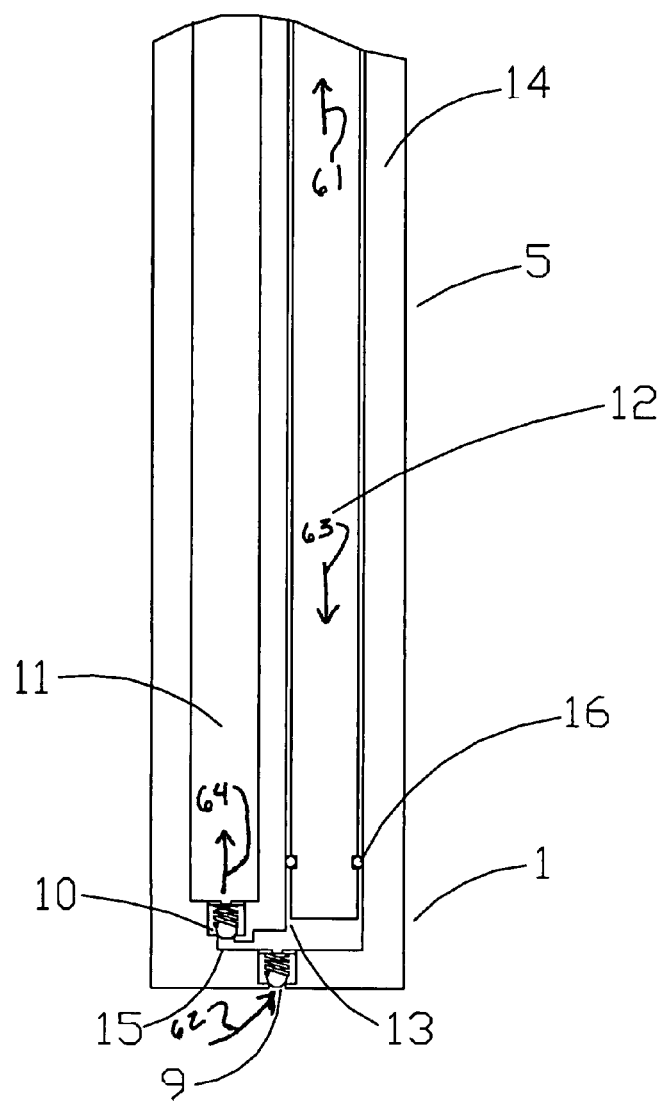
FIG. 2 is a side, partially cut-away, partially cross sectional view of a preferred embodiment of a plunger/check valve pump design of the present invention.

Another pump design, shown in FIG. 2, illustrates a plunger and check-valve type of pump could also be inserted into the process for sampling at prevailing pressure and temperature, in the manner illustrated in FIG. 1.

The pump 5 is comprised of housing 14, housing bottom 15, first end of insertable composite sampler pump 1, intake valve 9, outlet valve 10, outlet passage 11, pump piston 12, sample metering cavity 13, and pump piston seal 16.

In operation, when pump piston 12 is actuated upward 61, sample fluid enters sample metering chamber 13 through 62 intake valve 9. When pump piston 12 is actuated downward, sample fluid from sample metering chamber 13 flows 64 through outlet valve 10, outlet passage 11, to a sample container. When pump piston 12 is actuated upward 61, intake valve 9 is open and outlet valve 10 is closed. When piston pump 12 is actuated downward 63, inlet valve 9 is closed and outlet valve 10 is open. The sample metering volume is controlled by pump piston 12 travel.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A device for obtaining a spot sample, comprising:
  a housing formed therein a sample cavity having first and second ends and a wall, said housing being formed so as to be immersed into a pressurized fluid process;
  a moveable end slidingly engaging said wall of said sample cavity, so as to form a moveable fluid barrier within said sample cavity, said moveable end slidably positionable from said second end of said cavity to said first end of said cavity, so as to provide in said cavity a variable volume associated with the position of said moveable barrier;
  a valve associated with said sample cavity, said valve having a passage communicating with said second end of said sample cavity, said valve comprising a stem/poppet, said stem/poppet formed to be situated adjacent to said moveable end when said moveable end is situated adjacent to said second end of said cavity and said valve is in a closed position, so as to form a minimum volume at said second end of said cavity;
  whereby, upon positioning said moveable end adjacent to said second end of said cavity to form a minimum volume at said second end of said cavity, and immersing said device into a pressurized fluid process so that said device reaches temperature equilibrium with said pressurized process, and opening said valve, said fluid passes through said valve, such that the pressurized fluid engages said moveable end so as to urge said moveable end from said second end of said cavity towards said first end of said cavity so as to increase the size of said cavity while, filling said cavity, while maintaining the spot sample at the prevailing pressure and temperature of the pressurized fluid process.

2. The device of claim 1, wherein there is further provided an insertion device to insert said housing into the pressurized fluid process.

3. The device of claim 1, wherein said pressurized fluid process is situated in a pipeline.

4. The method of obtaining a spot sample, comprising the steps of:
  a. providing a spot sample container, comprising:
    a housing having formed therein a sample cavity having first and second ends, and a wall;
    a moveable end slidingly engaging said wall of said sample cavity, so as to form a moveable fluid barrier within said sample cavity, having a variable volume associated with the position of said moveable barrier;
    a valve associated with said sample cavity said valve communicating with a passage situated at said second end of said sample cavity;
  b. inserting said container into a pressurized hydrocarbon fluid process;
  c. allowing the temperature of said container to reach equilibrium with the temperature of said pressurized fluid process placing said container at equal to or above the hydrocarbon dew point temperature, in order to prevent condensate from forming in said sample cavity;
  d. opening said valve;
  e. allowing fluid from said pressurized fluid process to migrate into said second end of said sample cavity at the prevailing temperature and pressure of said pressurized fluid process; while
  f. allowing said pressurized fluid process to engage said moveable stop to slidingly migrate from a minimum volume at said second end of said sample cavity to a maximum volume at said first end of said sample cavity as said sample cavity fills with fluid;
  g. closing said valve, providing a filled spot sample container.

5. The method of claim 4, wherein in step "a" said valve comprises a stem/poppet which is positionable in open and closed positions with the opening and closing of said valve, respectively, wherein, in its closed position, said stem/poppet is situated adjacent to said second end of said sample cavity; and wherein there is further provided the added step "a1" following step "a" comprising the steps of closing said stem/poppet of said valve and positioning said moveable end at said second end of said sample cavity, so as to provide minimum volume therebetween.

6. A method for receiving and storing a fluid sample comprising the steps of:
  a. inserting a fluid container into a fluid source until said fluid container reaches temperature equilibrium with said fluid source;
  b. allowing fluid to flow into said fluid container, providing a filled fluid container;
  c. sealing said filled fluid container;
  d. removing said filled fluid container from said fluid source.

7. The method of claim 6, wherein said fluid comprises hydrocarbon gas, and wherein, prior to step "a" there is provided the additional step "1" of evacuating said fluid container.

8. The method of claim 6, wherein said fluid container in step "a" comprises a sample cavity having first and second ends, and a valve situated at said second end of said sample cavity; and wherein there is provided the additional step 1 after step "a" of providing a moveable barrier in said sample cavity, and positioning said moveable barrier at said second end of said sample cavity adjacent to said valve, so as to provide a minimum volume within the sample cavity between said moveable barrier and valve prior to sampling.

9. The method of claim 6, wherein said fluid container has first and second ends and a valve situated said second end, said fluid container further comprising a storage volume and wherein, prior to step "a" there is provided the additional step "1" of providing in said fluid container a moveable barrier to vary the fluid storage volume from essentially zero volume to maximum volume.

10. The method of claim 9, wherein after step "1" there is provided the additional step "ii" of moving said moveable barrier in said fluid container to said second end of said fluid container so as to be situated adjacent to said valve, and closing said valve, so as to reduce said fluid storage volume to essentially zero volume.

11. The method of claim 10, wherein in step "b" there is further included the step of opening said valve so as to allow fluid flow into said fluid container, such that said moveable barrier is moved by said fluid flowing into said fluid container, altering said container from essentially zero volume to maximum volume.

12. A device for obtaining a spot sample, comprising:
 a housing having formed therein a sample cavity having a wall and first and second ends;
 a moveable barrier situated within said sample cavity,
 a valve situated at said second end of said sample cavity, said valve comprising a stem/poppet, said stem/poppet formed to be situated adjacent to said moveable end when said moveable end is situated adjacent to said second end of said cavity and said valve is in a closed position, so as to form a minimum volume at said second end of said cavity;
 whereby, upon positioning said moveable barrier at said second end of said sample cavity so as to be adjacent to said valve, so as to provide minimum volume in said sample cavity at said second end of said cavity; and thereafter inserting said housing into a pressurized fluid process and allowing said housing to reach temperature equilibrium with said process, and upon opening said valve, said fluid passes through said valve and into said sample cavity, so as to fill said sample with fluid from said pressurized fluid process at the prevailing pressure and temperature of said fluid process.

13. A fluid container, comprising:
 a body having walls forming a chamber, said chamber having first and second ends;
 an isolation barrier situated within said chamber, said isolation barrier having first and second sides, said isolation barrier formed to slidingly engage said walls forming said chamber;
 an inlet valve having a stem/poppet situated at said adjacent to second side of said isolation barrier when said valve is closed and said isolation barrier is situated at said second end of said chamber, so as to form minimal volume therebetween; and
 an end stop formed to engage said isolation barrier at a predetermined point in said chamber;
 whereby, upon urging said isolation barrier along the walls of said chamber to said first end of said chamber so as to displace fluid situated between said first side isolation barrier and said inlet valve, and upon inserting said fluid container into a pressurized fluid process and allowing said fluid container temperature to reach equilibrium with said pressurized fluid process, then opening said inlet valve and flowing a sample gas through said inlet valve, said second side of said isolation barrier restrains the flow of gas through said chamber, while said sample gas urges said isolation barrier to slidingly migrate along said walls forming said chamber toward said end of said chamber, until said isolation barrier encounters said end stop, so as to provide a chamber filled with said sample gas.

14. A method of sampling a gas, comprising the steps of:
 a. providing a fluid container comprising a body having walls forming a chamber having first and second ends;
 b. providing an isolation barrier slidingly situated within said chamber, said isolation barrier having first and second sides;
 c. providing an inlet valve at said second side of said isolation barrier;
 d. providing an end stop formed to engage said isolation barrier;
 e. positioning said isolation barrier adjacent to said inlet valve, so as to urge said isolation barrier to displace fluid situated between said second side of said isolation barrier and said inlet valve, inserting said fluid container into a pressurized fluid source, and allowing said fluid container to reach temperature equilibrium with the pressurized fluid source;
 f. flowing a sample gas through said inlet valve;
 g. utilizing said sample gas to urge said isolation barrier to slidingly migrate along the walls of said chamber toward said second end of said chamber so as to fill said chamber with said sample gas.

15. The method of claim 14, wherein in step "e" said pressurized fluid source is contained in a pipeline.

16. The method of claim 14, wherein in step "ei" an insertion device is utilized to insert said fluid container is the pressurized fluid source.

17. The method of claim 16, wherein in step "g" said pressurized fluid source is contained in a pipeline.

18. The method of claim 17, wherein in step "f" said sample gas flows from said pressurized fluid source at the prevailing pressure and temperature of said pressurized fluid source.

19. The method of claim 17, wherein there is provided after step "g" the additional steps "b" of closing said inlet valve so as to contain said sample gas in said chamber, and "l" removing said fluid container from said pressurized fluid source.

20. The method of claim 19, wherein between steps "g" and "h" there is provided the additional step "gi" of providing controlled flow of said sample gas into said fluid container via said isolation barrier slidingly migrating along the walls of said chamber, until said sample gas fills said chamber of said fluid container.

21. A device for obtaining a spot sample, comprising:
 a housing having formed therein a sample cavity having first and second ends and a wall;
 a valve associated with second end of said sample cavity, said valve comprising a stem/poppet; and
 a moveable fluid barrier within said sample cavity having a variable volume associated with the position of said moveable barrier;
 said stem/poppet formed to be situated adjacent to said moveable end when said moveable end is situated adjacent to said second end of said cavity and said valve is in a closed position, so as to form a minimum volume at said second end of said cavity;
 whereby, upon positioning said moveable barrier adjacent to said second end of said sample cavity so as to provide minimum volume between said valve and said barrier, and upon immersing said device into a pressurized fluid process until said device reaches temperature equilibrium with said process and opening said valve, said fluid passes through said valve and into said sample cavity, filling said sample cavity.

22. The device of claim 21, wherein there is further provided an insertion device for inserting said housing into the pressurized fluid process.

23. The device of claim 22, wherein said moveable barrier is slidingly engaged to said wall of said sample cavity.

24. The device of claim 23, wherein said pressurized fluid process is situated in a pipeline.

25. The device of claim 24, wherein upon said moveable barrier being slidably positioned at said first end of said sample cavity, said sample cavity is at maximum volume.

26. The method of obtaining a spot sample from a pressurized process gas, comprising the steps of:
   a. providing a spot sample container, comprising:
      a housing having formed therein a sample cavity having first and second ends, and a wall;
      a valve situated at said second end of said sample cavity;
   b. immersing said container into the pressurized process gas;
   c. waiting until said container reaches temperature equilibrium with said fluid source, then opening said valve;
   d. allowing said pressurized process gas to migrate into said sample cavity;
   e. closing said valve, providing a filled spot sample container.

27. The method of claim 26, wherein in step "a" there further comprises the additional step "a1" of providing a moveable fluid barrier within said sample cavity, having a variable volume associated with the position of said moveable barrier, and wherein after step "c" there is provided the additional step "c(1)" of allowing said moveable barrier to migrate from said second end of said sample cavity to said first end of said sample cavity as said sample cavity fills with gas.

28. The method of claim 27, wherein in step "a" said moveable fluid barrier slidingly engages said wall of said sample cavity, and in step "c(1)" said moveable barrier slidingly migrates from said second end of said sample cavity to said first end of said sample cavity as said sample cavity fills with gas.

29. The method of claim 28, wherein there is further provided after step "c" the additional step "f" of removing said filled spot sample container from said pressurized process gas.

30. The method of claim 29, wherein said pressurized process gas is contained in a pipeline.

31. A device for obtaining a spot sample from a pressurized hydrocarbon gas stream having a pressure and a temperature, comprising:
   a housing having formed therein a sample cavity having first and second ends;
   a valve situated at said second end of said sample cavity, said valve comprising a stem/poppet, said stem/poppet formed to be situated adjacent to said moveable end when said moveable end is situated adjacent to said second end of said cavity and said valve is in a closed position, so as to form a minimum volume at said second end of said cavity, and
   a moveable fluid barrier within said sample cavity having a variable volume associated with the position of said moveable barrier;
   whereby, upon positioning said moveable barrier adjacent to said second end of said sample cavity so as to provide minimum volume between said valve and said barrier, said hydrocarbon gas passes through said valve and into said sample cavity so as to fill said sample cavity at the prevailing pressure and temperature of said fluid process.

32. The device of claim 31, wherein inserting said device into said pressurized fluid process so as to bring said device and said pressurized fluid process into temperature equilibrium, and opening said valve, said pressurized process gas migrates into a minimum volume sample cavity so as to engage said moveable barrier to urge said moveable barrier to migrate from one end of said sample cavity to the other, so as to fill said sample cavity with said pressurized fluid process gas stream at prevailing pressure and temperature.

* * * * *

UNITED STATES PATENT AND TRADEMARK OFFICE
CERTIFICATE OF CORRECTION

| | |
|---|---|
| PATENT NO. | : 7,481,125 B2 |
| APPLICATION NO. | : 11/151018 |
| DATED | : January 27, 2009 |
| INVENTOR(S) | : Mayeaux |

It is certified that error appears in the above-identified patent and that said Letters Patent is hereby corrected as shown below:

Title Page,

Item (60), Related U.S. Application Data, please add:

Provisional Application No. 60/646,314 filed on Jan. 24, 2005

Signed and Sealed this

Thirty-first Day of March, 2009

JOHN DOLL
*Acting Director of the United States Patent and Trademark Office*